(12) United States Patent
Travis et al.

(10) Patent No.: US 11,698,368 B2
(45) Date of Patent: Jul. 11, 2023

(54) IDENTIFYING STATUS OF MALE FERTILITY BY DETERMINING SPERM CAPACITATION

(71) Applicant: Cornell University, Ithaca, NY (US)

(72) Inventors: Alexander J. Travis, Ithaca, NY (US); Gianpiero Palermo, New York, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 15/512,357

(22) PCT Filed: Sep. 16, 2015

(86) PCT No.: PCT/US2015/050377
§ 371 (c)(1),
(2) Date: Mar. 17, 2017

(87) PCT Pub. No.: WO2016/044392
PCT Pub. Date: Mar. 24, 2016

(65) Prior Publication Data
US 2017/0248584 A1    Aug. 31, 2017

Related U.S. Application Data

(60) Provisional application No. 62/051,536, filed on Sep. 17, 2014, provisional application No. 62/051,533, filed on Sep. 17, 2014.

(51) Int. Cl.
*G01N 33/50* (2006.01)
*G01N 33/68* (2006.01)

(52) U.S. Cl.
CPC ..... *G01N 33/5091* (2013.01); *G01N 33/5044* (2013.01); *G01N 33/689* (2013.01); *G01N 2800/367* (2013.01)

(58) Field of Classification Search
CPC ........... G01N 33/5091; G01N 33/5044; G01N 33/689; G01N 2800/367
See application file for complete search history.

(56) References Cited

U.S. PATENT DOCUMENTS

| 7,160,676 B2 | 1/2007 | Travis et al. |
| 8,367,313 B2 | 2/2013 | Travis et al. |
| 2010/0248302 A1 | 9/2010 | Travis et al. |

FOREIGN PATENT DOCUMENTS

| WO | 1998/000440 A1 | 1/1998 |
| WO | 2005009222 A2 | 2/2005 |
| WO | 2015/032842 A1 | 3/2015 |

OTHER PUBLICATIONS

Prakash et al. Preparation By Differential Gradient Centrifugation is Better Thn Swim-Up in Selecting Sperm With Normal Morphology (Strict Criteria); Fertility and Sterility, vol. 69, No. 4, pp. 722-726. (Year: 1998).*
Galantino-Homer et al. Effects of 2-Hydroxypropyl-Beta-Cyclodextrin and Cholesterol On Porcine Sperm Viability and Capacitation Status Following Cold Shock or Incubation; Molecular Reproduction and Development, vol. 73, pp. 638-650. (Year: 2006).*
Neri, Q. V., Testing the Effects of Cryopreservation on a Biomarker-Based Assay of Sperm-Function: Toward Generating a Standard for Semen Samples with Known Fertility, Fertility and Sterility, vol. 100, No. 3., p. 1048. Oct. 17, 2013.
Vairo, et al., Testing the Effects of Cryopreservation on a Biomarker-Based Assay of Sperm-Function: Toward Generating a Standard for Semen Samples with Known Fertility, Fertility and Sterility, vol. 100, No. 3., p. 248. Oct. 15, 2013.
Selvaraj, et al., GM1 Dynamics as a Marker for Membrane Changes Associated With the Process of Capacitation in Murine and Bovine Spermatoza, Journal of Andrology, vol. 28, No. 4, pp. 588-599. Jul. 2007.
Obembe, O.O., et al., Implication of Hongres 1 Protein in Quassin-Induced Male Reproductive Abnormality in Rats, Endocrinol. Metab. Synd. May 1, 2014, vol. 3, No. 2, pp. 1-7.
Park, Y., et al., Sperm Penetration Assay as an Indicator of Bull Fertility, Journal of Reproduction and Development, Apr. 12, 2012, vol. 58, No. 4, pp. 461-466.
Selvaraj, et al., GM1 Dyanmics indicate membrane changes associated with capacitation in murine spermatoza, Biology of Reproduction, p. 166. Jul. 1, 2007.
Hiroaki Shibahara, Obstetrical and Gynecological Examination, Journal of obstetrics and Gynecology, 2007, N29-N39,vol. 59, No. 4, Japan.

* cited by examiner

*Primary Examiner* — Melissa L Fisher
*Assistant Examiner* — Paul C Martin
(74) *Attorney, Agent, or Firm* — Hodgson Russ LLP

(57) ABSTRACT

This disclosure provides a method for determining male fertility status. The method comprises determining $G_{M1}$ distribution patterns following induced sperm capacitation, identifying the frequency of distribution of various patterns, and determining if the frequency distribution of certain $G_{M1}$ patterns in response to induced capacitation is altered. Based on the change in the frequency distribution patterns of certain patterns in response to induced capacitation, alone or in combination with other sperm attributes, male fertility status can be identified.

11 Claims, 4 Drawing Sheets

IDENTIFYING STATUS OF MALE FERTILITY BY DETERMINING SPERM CAPACITATION

CROSS-REFERENCE TO RELATED APPLICATIONS

This application claims priority to U.S. Provisional Application No. 62/051,533, filed on Sep. 17, 2014, and U.S. Provisional Application No. 62/051,536, filed on Sep. 17, 2014, the disclosures of which are incorporated herein by reference.

STATEMENT REGARDING FEDERAL FUNDING

This work was supported by funding under Grant Numbers R01 HD-045664, K01-RR00188, and DP1-EB016541 from the National Institutes of Health. The Government has some rights in the invention.

FIELD OF THE DISCLOSURE

This invention relates generally to the field of male fertility and more specifically to determining male fertility status based on $G_{M1}$ ganglioside distribution patterns following induced sperm capacitation.

BACKGROUND OF THE DISCLOSURE

In the US, 10% of couples have medical appointments related to infertility with 40% of infertility being associated with the male. Globally, this translates to over 73 million infertile couples. Typical male reproductive health exams assess sperm number, appearance, and motility. Unfortunately, half of infertile men have sperm that meet normal parameters for these descriptive criteria and are only identified as having "idiopathic infertility" after repeatedly failing at both natural conception and techniques of assisted reproduction such as intra-uterine insemination (IUI). Because each failed cycle inflicts great physical, emotional, and financial tolls on couples and it costs the US healthcare system over $5 billion annually, there is a tremendous need for a practical test of sperm function. Data on sperm function would allow clinicians to direct their patients toward a technology of assisted reproduction that would give them the best chance to conceive.

Upon entrance into the female tract, sperm are not immediately able to fertilize an egg. Rather, they must undergo a process of functional maturation known as "capacitation." This process relies upon their ability to respond to specific stimuli by having specific changes in their cell membrane, namely a change in the distribution pattern of the ganglioside $G_{M1}$ in response to exposure to stimuli for capacitation.

SUMMARY OF THE DISCLOSURE

A diagnostic method for male fertility status is disclosed. The method is based on observations that only certain $G_{M1}$ distribution patterns during induced sperm capacitation were indicative of male fertility status. In one aspect, this disclosure provides a method for identifying male fertility status based on a change in the frequency distribution of certain $G_{M1}$ patterns in response to induced capacitation.

In one embodiment, the method comprises obtaining a sperm sample (such as a semen sample) from an individual, exposing the sperm to the one or more stimuli that can induce capacitation, fixing the sperm in a fixative (such as an aldehyde fixative), determining $G_{M1}$ distribution pattern in the fixed sperm, determining if there is a change in the frequency distribution of certain patterns upon exposure to capacitation stimuli or if the frequency distribution of certain $G_{M1}$ patterns matches certain predetermined criteria, and based on the change in the frequency distribution and/or meeting of the distribution criteria, identifying fertility status of the individual.

Based on the $G_{M1}$ distribution patterns, individuals may be identified as having normal fertility status or abnormal fertility status, or may be designated into fertility categories. For example, individuals may be designated as "infertile," "sub-fertile," or "fertile" and these results may be used to inform patients and their physicians whether to try to conceive naturally, perform IUI, or proceed to in vitro fertilization (IVF) or intra-cytoplasmic sperm injection (ICSI). For example, if an individual is designated as infertile, a physician may advise the individual against continuing natural conception and/or IUI. In another example, if an individual is designated as sub-fertile and has a young female partner, a physician may advise to attempt IUI.

In one aspect, the present disclosure provides kits for determination of male fertility status. The kit comprises one or more of the following: non-capacitating media, capacitating media, fixative, reagents for determining distribution of $G_{M1}$ patterns, representations of $G_{M1}$ patterns that are useful for determination of fertility status, and comparison charts or predetermined criteria that provide correlative information between the patterns and fertility status.

BRIEF DESCRIPTION OF THE DRAWINGS

FIG. 2A), or capacitating conditions (normal semen-CAP; FIG. 2B), and localization patterns of $G_{M1}$ in human sperm from infertile males under capacitating conditions (ICSI-CAP; FIG. 2C). In the normal sperm, note the shift from the INTER pattern to the APM pattern and the AA pattern. In comparison with these normal data, sperm from a group of men known to have unexplained infertility were also subjected to the $G_{M1}$ assay. In these sperm (ICSI-CAP), there were almost no differences in the APM or AA patterns under capacitating conditions relative to the normal sperm incubated under non-capacitating conditions. These men with unexplained infertility had previously failed repeatedly at natural conception, IUI and/or classical IVF, and they were presenting for ICSI.

DETAILED DESCRIPTION OF THE DISCLOSURE

Figure 1:
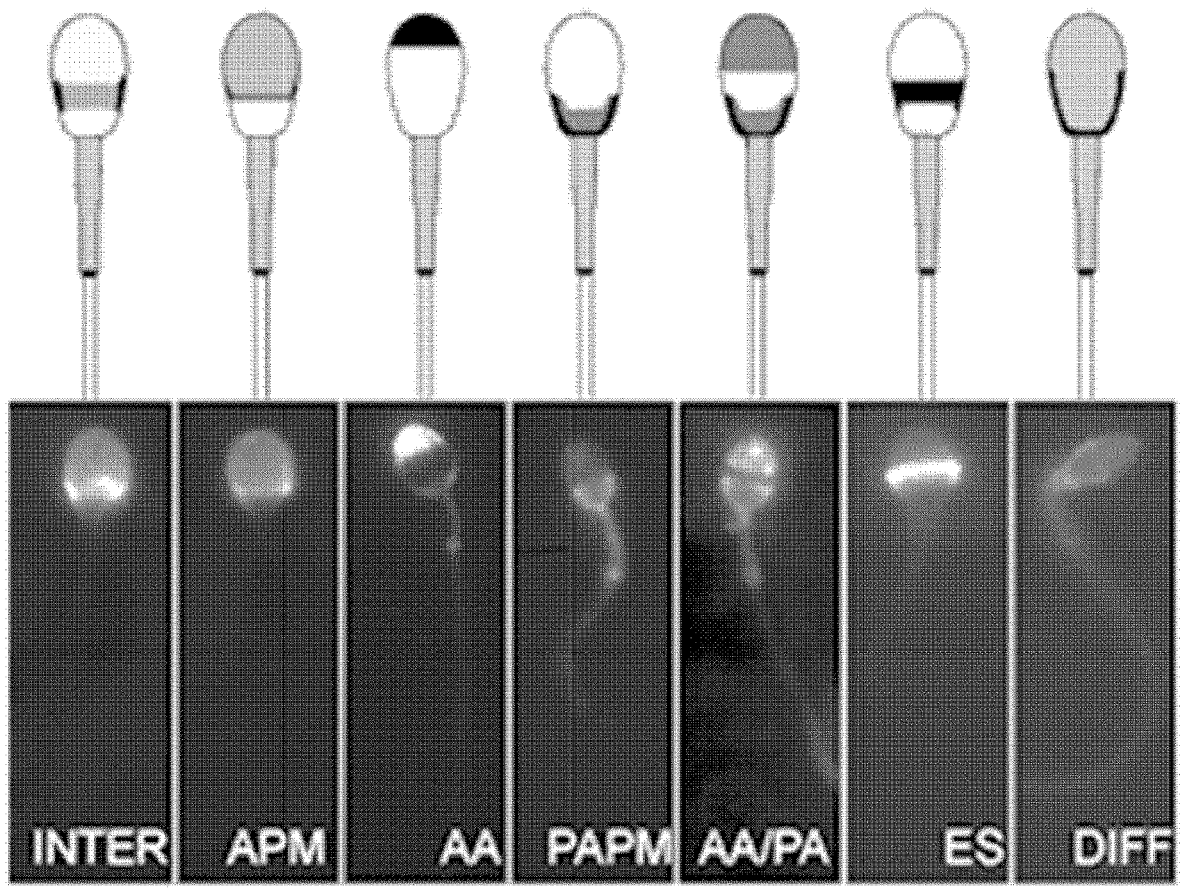
FIG. 1. Localization patterns of $G_{M1}$ in normal human sperm and sperm from infertile males under non-capacitating conditions or capacitating conditions.

The present disclosure is based on the observations that certain $G_{M1}$ distribution patterns can provide information regarding male fertility status. Determination of $G_{M1}$ patterns is described in U.S. Pat. Nos. 7,160,676, 7,670,763, and 8,367,313, the disclosures of which are incorporated herein by reference. This disclosure provides methods and kits for determination of male fertility status. The method is based on a change in the frequency of certain $G_{M1}$ patterns upon exposure to capacitating stimuli.

In one aspect, the disclosure provides a method for determining male fertility status. The method comprises subjecting a sperm sample from an individual to capacitating and non-capacitating conditions, determining a change in the frequency of certain $G_{M1}$ patterns upon exposure to capacitating conditions, and based on the level of change, identifying the fertility status.

The term "capacitated" sperm refers to sperm which have been incubated under conditions which promote the process of capacitation. Specifically, this requires the presence of bicarbonate and calcium ions in the medium, and the presence of a sterol acceptor such as serum albumin or a cyclodextrin. Capacitated sperm have acquired the ability to undergo acrosome exocytosis and have acquired a hyperactivated pattern of motility. Consequently, the term "non-capacitated" sperm refers to sperm which are not incubated with one or more of the above-listed stimuli for capacitation. Such sperm do not undergo acrosome exocytosis induced by a physiological ligand such as the zona pellucida, solubilized proteins from the zona pellucida, or progesterone. In addition, sperm incubated under non-capacitating conditions also will not demonstrate hyperactivated motility.

Capacitation may be induced in vitro by exposure to external stimuli such as bicarbonate and calcium ions, and mediators of sterol efflux such as 2-hydroxy-propyl-β-cyclodextrin, methyl-β-cyclodextrin, serum albumin, high density lipoprotein, phospholipids vesicles, liposomes, etc. An identifiable change in the $G_{M1}$ distribution pattern is observed when sperm are exposed to one or more of these stimuli in vitro.

After collection, human semen samples are typically processed in some way, including one or more of the following: liquefaction, washing, and/or enrichment. Liquefaction involves allowing the sample to liquefy at room temperature or at 37° C. (or any temperature therebetween) for various time periods (typically 15-20 minutes, but ranging from 10-60 minutes). Liquefaction is a process through which the seminal plasma converts from a gel into a more fluid/liquid consistency. Seminal plasma will typically liquefy without any manipulation but with especially viscous samples, or if there is a desire to hasten the process or make a consistent liquefaction protocol by which all samples are handled, one can also achieve this by adding various reagents such as proteolytic enzymes, reducing agents, or other mucolytic agents. These include, but are not limited to: α-chymotrypsin, α-amylase, dithiothreitol, pancreatic dornase, bromelain, papain, subtilisin, trypsin, and sputolysin. The sperm can be washed by centrifugation and resuspension and subjected to semen analysis, and/or be subjected to one or more selection processes including: layering on top of, and centrifugation through a density gradient; layering on top of, and centrifugation through a density gradient followed by collection of the sperm-enriched fraction followed by resuspension and washing; layering on top of, and centrifugation through a density gradient followed by collection of the sperm-enriched fraction and overlaying on top of that a less dense medium into which motile sperm will swim up; or overlaying a less dense medium on top of the sample and allowing motile sperm to swim up into it.

After initial processing, the sperm can be counted, and a given number of sperm can then be placed into containers (such as tubes) containing non-capacitating or capacitating medium to achieve desired final concentrations. In one embodiment, the final typical concentration of sperm is 1,000,000/ml (final concentration ranges might vary from 250,000/ml-250,000,000/ml). The base medium for incubating the sperm under non-capacitating and capacitating conditions can be a physiological buffered solution such as, but not limited to, human tubal fluid (HTF); modified human tubal fluid (mHTF); Whitten's medium; modified Whitten's medium; KSOM; phosphate-buffered saline; HEPES-buffered saline; Tris-buffered saline; Ham's F-10; Tyrode's medium; modified Tyrode's medium; TES-Tris (TEST)-yolk buffer; or Biggers, Whitten and Whittingham (BWW) medium. The base medium can have one or more defined or complex sources of protein and other factors added to it, including fetal cord serum ultrafiltrate, Plasmanate, egg yolk, skim milk, albumin, lipoproteins, or fatty acid binding proteins, either to promote viability or at concentrations sufficient to help induce capacitation. Typical stimuli for capacitation include one or more of the following: bicarbonate (typically at 20-25 mM, with ranges from 5-50 mM), calcium (typically at 1-2 mM, with ranges from 0.1-10 mM), and/or cyclodextrin (typically at 1-3 mM, with ranges from 0.1-20 mM). Cyclodextrins may comprise 2-hydroxy-propyl-β-cyclodextrin and/or methyl-β-cyclodextrin. Incubation temperatures are typically 37° C. (ranging from 30° C.-38° C.), and incubation times are typically 1-4 hours (ranging from 30 minutes to 18 hours), though baseline samples can be taken at the start of the incubation period ("time zero").

For generating patterns of $G_{M1}$, the sperm are typically washed with a standard base medium (e.g., phosphate-buffered saline, Modified Whitten's medium, or other similar media) and incubated with an affinity molecule for $G_{M1}$ which has a detectable moiety on it. Since $G_{M1}$ has extracellular sugar residues which can serve as an epitope, it can be visualized without having to fix and permeabilize the cells. However, fixation of the cells results in better preservation of the specimen, easier visualization (compared to discerning patterns in swimming sperm) and allows longer visualization time, while contributing to pattern formation. Various fixatives known for histological study of spermatozoa are within the purview of those skilled in the art. Suitable fixatives include paraformaldehyde, glutaraldehyde, Bouin's fixative, and fixatives comprising sodium cacodylate, calcium chloride, picric acid, tannic acid and like. In one embodiment, paraformaldehyde, glutaraldehyde or combinations thereof are used.

Fixation conditions can range from 0.004% (weight/volume) paraformaldehyde to 4% (weight/volume) paraformaldehyde, although 0.01% to 1% (weight/volume) paraformaldehyde is typically used. In one embodiment, 0.005% (weight/volume) paraformaldehyde to 1% (weight/volume) paraformaldehyde can be used. In one embodiment, 4% paraformaldehyde (weight/volume), 0.1% glutaraldehyde (weight/volume) and 5 mM $CaCl_2$ in phosphate buffered saline can be used.

The distribution pattern of $G_{M1}$ in live or fixed sperm can be obtained by using affinity binding techniques. A molecule having specific affinity for the $G_{M1}$ ganglioside can be used. The affinity molecule can be directly linked to a detectable label (such as a fluorophore) or may be detected by a second affinity molecule which has a detectable label on it. For example, the b subunit of cholera toxin is known to specifically bind to $G_{M1}$. Therefore, a labeled (such as fluorescent labeled) cholera toxin b subunit can be used to obtain a pattern of distribution of $G_{M1}$. Typical final concentrations of the b subunit of cholera toxin linked to fluorophore are 10-15 μg/ml, though concentrations can range from 0.1-50 μg/ml. Alternatively, a labeled antibody to $G_{M1}$ can be used. In yet another alternative, a labeled antibody to the cholera toxin b subunit can be used to visualize the pattern of $G_{M1}$ staining. And in yet another alternative, a labeled secondary antibody which binds to either the primary antibody that binds directly to $G_{M1}$ or to the primary antibody that binds to the b subunit of cholera toxin could be used. The term "$G_{M1}$ staining" or "staining of $G_{M1}$" or "labeling" or related terms as used herein means the staining seen on or in cells due to the binding of labeled affinity molecules to $G_{M1}$. For example, when fluorescent tagged Cholera toxin b subunit is used for localization of $G_{M1}$, the signal or staining is from the Cholera toxin b subunit but is indicative of the location of $G_{M1}$. The terms "signal" and "staining" and "labeling" are used interchangeably. The detectable label is such that it is capable of producing a detectable signal. Such labels include a radionuclide, an enzyme, a fluorescent agent or a chromophore. Labeling (or staining) and visualization of $G_{M1}$ distribution in sperm is carried out by standard techniques. Affinity molecules other than the b subunit of cholera toxin can also be used. These include polyclonal and monoclonal antibodies. Specific antibodies to $G_{M1}$ ganglioside can be generated by routine immunization protocols, or can be purchased commercially (e.g., Matreya, Inc., State College, Pa.). The antibodies may be raised against $G_{M1}$ or, can be generated by using peptide mimics of relevant epitopes of the $G_{M1}$ molecule. Identification and generation of peptide mimics is well known to those skilled in the art. In addition, the binding of the b subunit to cholera toxin might be mimicked by a small molecule. Identification of small molecules that have similar binding properties to a given reagent is well known to those skilled in the art.

For human sperm, seven different patterns (see details under Example 1) were observed. These patterns are designated as INTER, APM, AA, PAPM, AA/PA, ES, and DIFF. The $G_{M1}$ patterns are shown in FIG. 1 and further described below:

INTER: The vast majority of the fluorescence is in a band around the equatorial segment, with some signal in the plasma membrane overlying the acrosome. There is usually a gradient of signal, with the most at the equatorial segment and then progressively less toward the tip. There is often an increase in signal intensity on the edges of the sperm head in the band across the equatorial segment.

APM (Acrosomal Plasma Membrane): Compared to INTER there is less distinction in this pattern between the equatorial signal and that moving toward the apical tip. That is, the signal in the plasma membrane overlying the acrosome is more evenly distributed. APM signal is seen either from the bright equatorial INTER band moving apically toward the tip, or it can start further up toward the tip and be found in a smaller region, as it is a continuum with the AA.

AA (Apical Acrosome): In this pattern, the fluorescence is becoming more and more concentrated toward the apical tip, increased in brightness and reduced in area with signal.

PAPM (Post Acrosomal Plasma Membrane): Signal is exclusively in the post-acrosomal plasma membrane.

AA/PA (Apical Acrosome/Post Acrosome): Signal is both in the plasma membrane overlying the acrosome and post-acrosomal plasma membrane. Signal is missing from the equatorial segment.

ES (Equatorial Segment): Bright signal is seen solely in the equatorial segment. It may be accompanied by thickening of the sperm head across the equatorial region.

DIFF (Diffuse): Diffuse signal is seen over the whole sperm head.

It was observed that while the INTER, AA, APM patterns, and combinations of these patterns, correlate positively with viable sperm with normal sperm membrane architecture and therefore fertility, the PAPM, AA/PA, ES, and the DIFF patterns do not positively correlate with viability, normal membrane architecture and fertility. If incubated under non-capacitating conditions, the majority of viable sperm with normal membrane architecture will exhibit the INTER pattern, which is characterized by the majority of labeling being near the equatorial segment, with the rest extending through the plasma membrane overlying the acrosome. There is an increase in the frequency of the APM and AA patterns upon exposure to stimuli for capacitation. The APM pattern shows more uniform signal in the plasma membrane overlying the acrosome, whereas the AA pattern shows increasing intensity of signal in the rostral part of the sperm head, the apical acrosome, and reduced signal moving caudally toward the equatorial segment. It is considered that non-capacitated $G_{M1}$ distribution patterns for infertile individuals is similar to the patterns for non-capacitated normal individuals.

In one embodiment, the method comprises exposing an aliquot from a sperm sample from an individual to non-capacitating conditions and another aliquot from the same sample or a different sample from the same individual to capacitating conditions, fixing both sets of sperm, staining both sets of sperm to identify $G_{M1}$ patterns, determining the frequency of certain $G_{M1}$ patterns in both, determining if there is a change in the frequency of certain patterns upon exposure to capacitating conditions (by comparison to frequency under non-capacitating conditions), and identifying the fertility status based on the change in the frequency of the patterns. In one embodiment, the patterns are one or more of AA, APM, and INTER.

In one embodiment, the method comprises exposing a sperm sample from an individual to capacitating conditions, fixing the sperm, staining the sperm to identify $G_{M1}$ patterns, determining frequency of certain patterns and comparing the frequency of certain patterns to a control (i.e., a reference), and based on the comparison, identifying the fertility status. The control may be from a fertile individual, or may be from an individual known to be sub-fertile or infertile. In one embodiment, the controls are exposed to the same capacitation stimuli and fixative. In one embodiment, the control samples may be run in parallel to the test sample. In another embodiment, the control comparison might be made against the relative frequencies of different patterns found in sperm of populations of men who are either fertile, sub-fertile, or infertile.

Based on the results of the comparison, the fertility status of the male's sample can be established. The fertility status may be used by a clinician to inform the individual (or in the case of a non-human male, the owner or responsible party) regarding the likelihood of achieving pregnancy by different means of fertilization.

The male individual may be a human or a non-human animal. In the case of a non-human animal, identification of patterns that are correlated with fertility status can be carried out based on the teachings provided herein. Non-human animals include horse, cattle, dog, cat, swine, goat, sheep, deer, rabbit, chicken, turkey, various species of fish and various zoological species.

In one embodiment, the method of this disclosure provides a method for designating a male as likely infertile comprising obtaining $G_{M1}$ distribution patterns in the sperm from the individual and from a normal control that have been incubated under capacitating and non-capacitating conditions and optionally fixed, and comparing the $G_{M1}$ distribution patterns. In the normal control, a statistically significant change in the percentage of sperm displaying certain patterns would be observed. If the same change is not observed in the sperm from the test individual, then the individual is designated as having an abnormal fertility status. In one embodiment, the patterns that are informative of normal and abnormal fertility status are patterns INTER, AA and/or APM. Thus, in a sample from an individual who is known to have a normal fertility status (which may be used as a control), there is an increase in the frequency of sperm exhibiting AA and/or APM patterns, and a decrease in the frequency of sperm exhibiting the INTER pattern upon exposure to capacitating conditions. If no change, or no significant change, is observed in the percentages of one or more of these patterns upon exposure to capacitating conditions, then the individual is designated as having fertility problems.

In a variation of the above embodiment, the control may be from an individual known to be infertile or sub-fertile. In this embodiment, if the changes in $G_{M1}$ patterns from the test individual upon capacitation in the INTER, AA and/or APM patterns are the same as the control, then the individual can be deemed as sub-fertile or infertile.

In yet another variation of the above embodiment, the sample from a test individual may be evaluated without comparing to a control. If no change, or no significant change, is observed in the frequency of INTER, AA and/or APM distribution patterns upon exposure to capacitating conditions, then the individual may be deemed as abnormal and may be designated for further testing, whereas if changes are observed such that INTER is decreased, AA is increased, and/or APM is increased, then the individual may be designated as having normal fertility.

In one embodiment, the method comprises analysis of $G_{M1}$ distribution patterns to identify frequency of AA and APM patterns in sperm exposed to capacitating conditions. The frequency can be expressed as a percentage of one or more of the $G_{M1}$ distribution patterns relative to the total. In one embodiment, fertility is predicted based on a comparison of the frequency of AA and/or APM distribution patterns against a predetermined fertility threshold, for example, the threshold (i.e., cut-off) level between individuals classified as infertile and sub-fertile, or the threshold level between individuals classified as sub-fertile and those classified as fertile. A threshold can also be used to distinguish high relative fertility versus low relative fertility. In an example, a relative percentage greater than or equal to 40 percent for the sum of AA and APM patterns is indicative of a high likelihood of fertility, while a level less than 40 is indicative of a low chance of fertility. In other embodiments, the fertility threshold level is within the range of 35-40 (relative percentage of AA+APM), inclusive. In other embodiments, the fertility threshold is 38, 38.5, 39, or 39.5.

In one embodiment, a similar threshold can be established for the INTER pattern, for the AA or the APM patterns alone, or for any combination of the INTER, AA or APM patterns.

In general, a control is considered to be fertile if the likelihood of achieving fertilization/clinical pregnancy is greater than, for example, 50% within 3 or fewer cycles. Individuals may be considered to be fertile if the likelihood of achieving fertilization/clinical pregnancy is above some classification value. For example, an individual may be classified as "fertile" if the likelihood of achieving fertilization/clinical pregnancy is greater than 50% within 3 or fewer cycles. In other embodiments, the fertile cut-off probability may be a value in the range of 50%-85%, inclusive.

In other embodiments, the fertility threshold is the value of AA and/or APM at which the fertility of a population ceases to substantially increase for increasing levels of AA and/or APM. Individuals may be designated as "infertile," "sub-fertile," or "fertile" based on the individual's level of AA and/or APM.

In some embodiments, the cut-off(s) for different fertility designations is/are determined from a set of data comprising the AA and/or APM frequencies and corresponding fertility success rates for a population of individuals (the percentage of successful fertilization for individuals having AA and/or APM values greater than or equal to a corresponding value). For example, the set of data may include an AA+APM value of 40 and a corresponding fertility success rate for individuals having an AA+APM greater than or equal to 40. The fertility threshold may be determined by trends and/or discontinuities in the set of data. For example, a region where the fertility success rate of the individuals does not substantially increase for increasing levels of AA+APM may exist below a level of roughly 14.5-18.5. Individuals having a level of AA+APM in this substantially flat region (<14.5-18.5) can be classified as infertile. The AA and/or APM level where the fertility of individuals begins to rise can be considered the infertility threshold level—i.e., the level separating those classified as infertile and those classified as sub-fertile. A region showing significant changes in fertility exists between this infertility threshold and a level of roughly 38-39, wherein the fertility again levels-off. This upper value can be considered a fertility threshold level—i.e., the level separating those classified as sub-fertile and those classified as fertile. In this way, the fertility threshold level may be the value of AA and/or APM wherein fertility of a population ceases to substantially increase for increasing levels of AA and/or APM.

In embodiments, fertility may be considered to substantially increase if the change in fertility, for a percentage point change in $G_{M1}$ frequency, is greater than 3%, 4%, 5%, 10%, or 15%. Other changes considered to be substantial will be apparent to those having skill in the art in light of the disclosure and are considered within the scope of the disclosure.

In other embodiments, the fertility threshold level may be a minimum level of AA and/or APM at which the fertility of individuals is at least some value in the range of 60%-85% (wherein the value is chosen to be indicative of individuals classified as fertile). While specific reference is made to percentages or ranges for AA and/or APM, it will be apparent that similar determinations may be made from changes in the INTER pattern or from a combination of one or more of INTER, AA and APM patterns.

Figure 4:
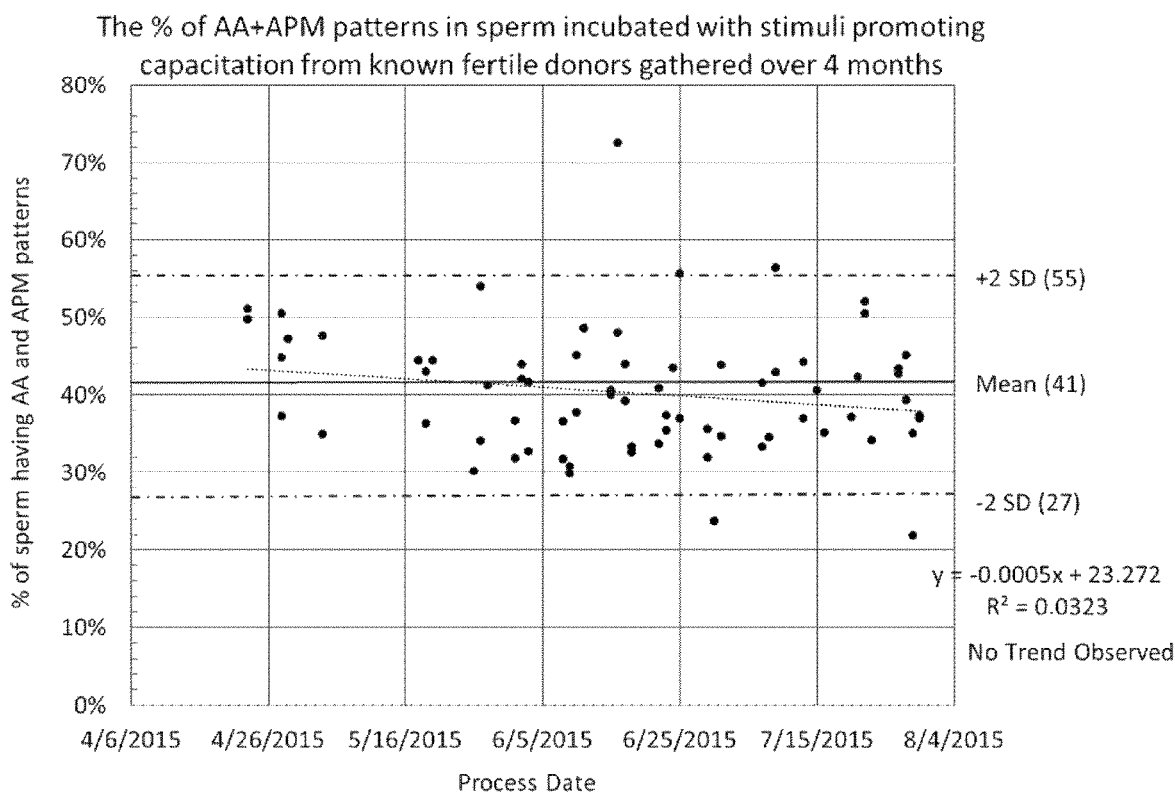
FIG. 4 shows the percentage of AA and APM patterns in sperm from known fertile donors incubated with stimuli promoting capacitation. The mean percentage of 41 percent is designated with a solid line. Two standard deviations above and below the mean (55 percent and 27 percent, respectively) are designated with dash-dot lines. In this example, two standard deviations below the mean was selected as an infertility threshold—i.e., sperm showing AA and APM patterns at below the 27 percent rate correlate to infertility.

In other embodiments, fertility thresholds may be determined by statistical analysis of the patterns found in sperm from a population of men, for example, 10 or more men, with known fertility. As shown in FIG. 4, 73 semen samples were obtained from 24 men known to be fertile. Their sperm was incubated with stimuli for capacitation, in this case 4 mM 2-hydroxy-propyl-β cyclodextrin, fixed with 0.01% paraformaldehyde (final concentration). The percentage of cells having patterns indicative of having capacitated (e.g., AA+APM) was assessed. The mean percentage of sperm having the AA and APM patterns was 41%, and 2 standard deviations from the mean was calculated as 27% and 55%.

In many diagnostic tests, 2 standard deviations from the mean is used to distinguish normal values from abnormal values. In this case, the value of 27% marking two standard deviations below the mean was selected as a threshold to distinguish infertile samples (i.e., those having scores of 27 or below), from sub-fertile samples (those scoring between 28-34, which is one standard deviation below the mean), versus fertile (those scoring within one standard deviation of the mean, or above). As such, an exemplary fertility threshold, to distinguish sub-fertile samples from fertile samples, can be a percentage of AA+APM patterns one standard deviation below a mean percentage of AA+APM patterns. Other thresholds may be selected. For example, the infertile/sub-fertile threshold may be selected as 3 standard deviations below the mean, and the sub-fertile/fertile threshold may be 2 standard deviations below the mean.

Figure 5:
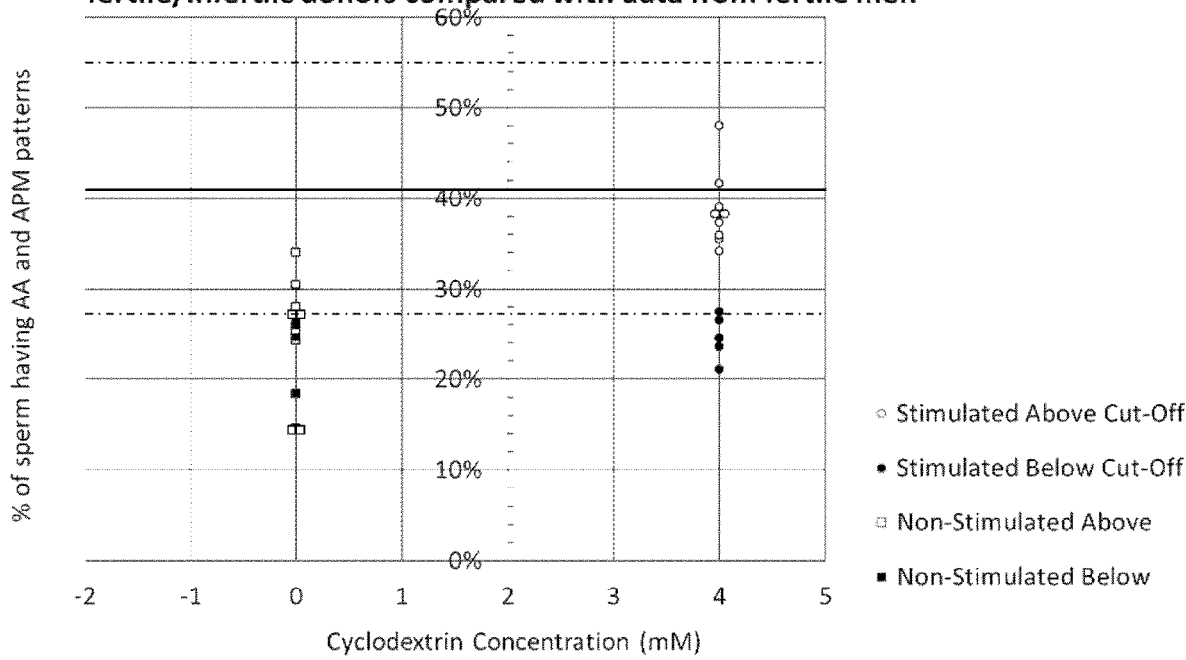
FIG. 5 compares the percentage of AA and APM patterns in sperm from suspected sub-fertile/infertile donors with the statistical thresholds of fertile men. The percentage of AA and APM patterns in sperm was measured under both capacitating (those points clustered at 4 mM cyclodextrin concentration) and non-capacitating conditions (those points clustered at 0 mM cyclodextrin concentration). Under the capacitating conditions, sperm were incubated with 4 mM 2-hydroxy-propyl β cyclodextrin. Based on the data in FIG. 4, the mean percentage of sperm having AA and APM patterns in fertile males of 41 percent is designated with a solid line. Two standard deviations above and below the mean (55 percent and 27 percent, respectively) are designated with dash-dot lines. Sperm showing AA and APM patterns at below the 27 percent rate correlate to infertility.

$G_{M1}$ localization patterns in 14 samples from 14 men seeking medical evaluation of their fertility status were analyzed. The relative percentages of sperm having AA+APM localization patterns were compared against the statistical thresholds identified from the population of known fertile men (FIG. 5). There were no differences observed in the samples incubated under baseline (non-stimulating, non-capacitating conditions). However, 5 of the 14 men produced samples that showed low percentages of sperm with AA+APM patterns when incubated with 4 mM 2-hydroxy-propyl β cyclodextrin. These 5 samples all fell below 2 standard deviations from the mean. It is believed that approximately 30-50% of couples having difficulty conceiving have a component of male factor. These data fall within that expected range.

In one aspect, the present disclosure provides kits for determination of male fertility status. The kit comprises one or more of the following: agents that can act as stimuli for capacitation, capacitating media, non-capacitating media, fixative, reagents for determining distribution of $G_{M1}$ patterns, representations of $G_{M1}$ patterns that are useful for determination of fertility status, and comparison charts that provide correlative information between the patterns and fertility status, or predetermined criteria that provide correlative information between the test values and fertility status. In one embodiment, the kit comprises non-capacitating and capacitating media, pattern charts (such as FIG. 1), containers etc. In one embodiment, the kit comprises an agent having 4% cyclodextrin to stimulate capacitation.

In one embodiment, the capacitating media comprises: modified human tubal fluid with added 2-hydroxy-propyl β cyclodextrin so as to give a 3 mM final concentration; the non-capacitating media comprises modified human tubal fluid; the fixative is 1% paraformaldehyde; and the reagent for determining $G_{M1}$ patterns is cholera toxin's b subunit (15 μg/ml final concentration). In other embodiments, the final concentration of paraformaldehyde is 0.01%.

An exemplary kit comprises modified HTF medium with gentamicin buffered with HEPES (Irvine Scientific, reference 90126). No difference in $G_{M1}$ localization scores, viability or sperm recovery, and capacitation was observed whether bicarbonate- or HEPES-buffered medium was used. Therefore, bicarbonate buffered media can also be used. Use of the HEPES-buffer enables the assay to be performed in clinics using air incubators or water baths, as opposed to only being compatible with $CO_2$ incubators. Similarly, adding supplemental proteins, whether commercial (HTF-SSSTm, Irvine Scientific, or plasmanate), or powdered albumin did not alter recovery or viability, and favorably enhance capacitation status.

The exemplary kit can further comprise cell isolation media (such as Enhance S-Plus Cell Isolation Media, 90% from Vitrolife, reference: 15232 ESP-100-90%). The exemplary reagents, consumables and procedures were demonstrated to yield advantageous labeling of $G_{M1}$ on human sperm.

The exemplary kit can further comprise large orifice pipet tips (200 μl large orifice tip, USA scientific, 1011-8400). The exemplary kit can further comprise large orifice transfer pipets (General Purpose Transfer Pipets, Standard Bulb reference number: 202-20S. VWR catalog number 14670-147).

The exemplary kit can further comprise 1.5 ml tubes (Treatment cap, noncap, CD) (USA Scientific14159700)—one containing cyclodextrin in powdered form to stimulate capacitation, and one empty for noncapacitating conditions of media alone. In some embodiments, it is possible that the cyclodextrin will be found in a separate tube, to which medium will be added to make a stock solution, that itself would be added to the capacitating tube.

When isolating sperm from seminal plasma it is common for human andrology labs to collect sperm using density gradients. The exemplary kit can further comprise density gradient materials and/or instructions to remove the seminal plasma off the density gradient and then to collect the pelleted sperm using a fresh transfer pipette.

The exemplary kit can further comprise the fixative (such as 0.1% PFA), and optionally comprises informational forms (such as patient requisition form), labels and containers/bags/pouches and the like useful for shipping, storage or regulatory purposes. For example, the kit can contain a foil pouch, a biohazard bag with absorbent for mailing patient sample, a re-sealable bag with absorbent, and a foam tube place holder.

In another aspect, a method for measuring the fertility of a male individual is provided. The $G_{M1}$ localization assay can show whether sperm can capacitate, and therefore become competent to fertilize an egg. As described above, the assay may be scored as percentages of the morphologically normal sperm that have specific patterns of $G_{M1}$ localization in the sperm head. The APM and AA patterns increase as sperm respond to stimuli for capacitation. Cut-offs can be used to distinguish the relative fertility of the ejaculates, separating the semen samples into groups based on male fertility (i.e., distinguishing fertile from sub-fertile from infertile men). However, because sperm number, motility, and morphology can also influence male fertility, the present disclosure provides methods for creating an index of male fertility (the "male fertility index" or "MFI") that encompasses CAP score and one or more relevant semen parameters (e.g., number, motility, and morphology, etc.) CAP score (also referred to as $G_{M1}$ score) is the frequency of one or more $G_{M1}$ distribution patterns. For example, a CAP score can be a frequency of one or more of INTER, AA, and APM. Different indices can be generated that emphasize specific semen parameters. For example, indexes according to the present disclosure include:

CAP score×% with progressive motility×absolute number;

CAP score×% morphologically normal sperm×absolute number;

CAP score×% total motility×absolute number×% morphologically normal sperm; and other variations or combinations of CAP score and these parameters, or other specific parameters including those obtained using CASA (computer assisted sperm analysis), such as: VSL (velocity straight line); STR (straightness); LIN (Linearity); VCL (curvilinear velocity); VAP (velocity average path); % motility; duration of motility; LHA (lateral head amplitude); WOB (wobble); PROG (progression); and BCF (Beat cross frequency), etc. See, e.g., World Health Organization, "WHO Laboratory Manual for the Examination and Processing of Human Sperm," (Fifth Ed. 2010).

The male fertility index may be embodied as a method for measuring the fertility status of a male individual. A sperm sample is obtained, wherein the sperm sample is from the individual being measured and wherein at least a portion of the sperm sample has been exposed to capacitating conditions, exposed to a fixative, and stained for $G_{M1}$, as described above. The values of one or more semen parameters are obtained for the sperm sample, such as, for example, the volume of the original sample from the individual, and/or the concentration, motility, and/or morphology of the sperm of the sample. An MFI is determined from the frequency of one or more $G_{M1}$ distribution patterns (i.e., the "CAP" score) and the one or more obtained semen parameter values. In the examples used herein, the CAP score is the frequency of one or more $G_{M1}$ distribution patterns under capacitating conditions at three hours, but other variants of CAP scores will be apparent in light of this disclosure (e.g., frequency at other time intervals, change in frequency of a $G_{M1}$ pattern in capacitated from non-capacitated, etc.)

In an example, a male fertility index score was calculated for a sample of men using the CAP score for AA+APM, the volume, concentration, motility, and morphology, according to the following equation:

$$MFI = CAP\ Score \times Volume \times Concentration \times \frac{\%\ motility}{100} \times \frac{\%\ morphology}{100},$$

where the % motility is the percentage of sperm that are motile and the % morphology is the percentage of sperm that are morphologically normal. In the test, the average MFI for 26 individuals who had <40 as their $G_{M1}$ score at 3 hours (i.e., using a 40 cut-off for pass/fail), was 0.37, with a range from 0.04-0.95. Only 2 in this group had values of 0.75 or higher. The average MFI for the 7 individuals with a $G_{M1}$ score >/=39.5 at 3 hours (i.e., using a 40 cut-off for pass/fail), was 1.02, with a range from 0.23-2.79. Four individuals in this group scored higher than 0.75. Of those, three were fertile within three cycles, and the 4th was fertile on the 4th try. There was not a significant difference in sperm numbers or other semen analysis parameters between the two groups: (107.16 million sperm/ejaculate in the 26 who failed vs 127.7 million sperm/ejaculate in the 7 that passed; average morphology score of 3.73 in those that failed vs 3.14 in those that passed; and average motility of 46.89 in those that failed vs 51.86 in those that passed).

The male fertility index may be generated by a lab that reads the $G_{M1}$ localization assay. The lab may obtain a sperm sample, and a semen analysis corresponding to the sperm sample, from one or more facility (e.g., fertility clinic, sperm bank, etc.). Semen analysis information can be included on a card included with a $G_{M1}$ localization assay kit, sent electronically to the lab, and/or otherwise provided. In another exemplary embodiment, the lab obtains the CAP score of a sperm sample and also obtains the semen analysis information for the sperm sample. The lab calculates the male fertility index based on the obtained CAP score and the obtained semen analysis data.

An exemplary method for identifying fertility status of a human male individual comprises exposing sperm sample from the individual to non-capacitating and capacitating conditions. The sperm are fixed and a frequency of selected $G_{M1}$ patterns in the fixed sperm is determined. The frequency distributions for different $G_{M1}$ patterns in sperm exposed to non-capacitating and capacitating conditions is compared. A change in the frequency distribution of one or more selected $G_{M1}$ patterns in sperm exposed to capacitating conditions over sperm exposed to non-capacitating conditions is indicative of the fertility status of the individual. The selected $G_{M1}$ patterns can be INTER, AA and/or APM.

An exemplary method for identifying fertility status of a human male individual comprises exposing a sperm sample from the individual to capacitating conditions. The sperm are fixed and a frequency of selected $G_{M1}$ patterns in the fixed sperm is determined. The frequency distributions for different $G_{M1}$ patterns is compared to the frequency distributions from a control, wherein the control sperm sample has been exposed to the same capacitating conditions and same fixative. A change in the frequency distribution of one or more selected $G_{M1}$ patterns relative to the change in the control is indicative of different fertility status of the individual than the fertility status of the control. The $G_{M1}$ patterns can be INTER, AA and/or APM.

In the exemplary method, the control can be a sperm sample from an individual who is known to have normal fertility status or an individual who is known to have abnormal fertility status. The control can be a value obtained from a dataset comprising a plurality of individuals, for example, a dataset comprising at least 50 individuals.

An exemplary method for identifying fertility status of a human male individual as infertile, sub-fertile, or fertile, comprises exposing a sperm sample from the individual to capacitating conditions. $G_{M1}$ distribution patterns in the sample are determined. The frequency of one or more $G_{M1}$ patterns is compared to a fertility threshold wherein a frequency less than the fertility threshold is indicative of fertility problems. For example, a frequency less than the fertility threshold can be indicative of a fertility status of infertile or sub-fertile. The $G_{M1}$ distribution patterns can be INTER, AA and/or APM.

The capacitating conditions in the exemplary methods can include exposure to i) bicarbonate and calcium ions, and ii) mediators of sterol efflux such as 2-hydroxy-propyl beta cyclodextrin, methyl-β-cyclodextrin, serum albumin, high density lipoprotein, phospholipids vesicles, fetal cord serum ultrafiltrate, fatty acid binding proteins, or liposomes. In the exemplary methods, exposure of the control to capacitating or non-capacitating conditions can be done in parallel with the test sample.

An exemplary method for identifying fertility status of a human male individual as infertile, sub-fertile, or fertile, comprises exposing a sperm sample from the individual to capacitating conditions. The $G_{M1}$ distribution patterns in the sample is determined. The frequency of one or more $G_{M1}$ patterns is compared to an infertility threshold wherein a frequency less than the infertility threshold is indicative of fertility problems. For example, a frequency less than the infertility threshold can be indicative of a fertility status of infertile. The capacitating conditions in the exemplary method can include exposure to i) bicarbonate and calcium ions, and ii) mediators of sterol efflux such as 2-hydroxy-propyl beta cyclodextrin, methyl-β-cyclodextrin, serum albumin, high density lipoprotein, phospholipids vesicles, fetal cord serum ultrafiltrate, fatty acid binding proteins, or liposomes. The one or more $G_{M1}$ patterns can be INTER, AA and/or APM.

The fertility threshold in the exemplary methods can be the AA+APM pattern frequency at which the fertility of a population ceases to substantially increase. For example, the fertility threshold can be a level of AA+APM at which more than 50% of the population are fertile; a level of AA+APM at which more than 60-85% of a population is fertile; or a level of AA+APM in the range of 35-40 (relative percentage of total $G_{M1}$ patterns), inclusive. The fertility threshold can be 38, 38.5, 39, or 39.5% AA+APM (relative to total $G_{M1}$ patterns).

An exemplary method may further comprise comparing the frequency of one or more $G_{M1}$ patterns to an infertility threshold wherein a frequency less than the infertility threshold is indicative of infertility. For example, the infertility threshold can be the AA+APM pattern frequency at which the fertility of a population begins to substantially increase; a level of AA+APM at which less than 50% of the population are fertile; a level of AA+APM at which more than 60-85% of a population is fertile; or a level of AA+APM in the range of 14-18 (relative percentage of total $G_{M1}$ patterns), inclusive. The infertility threshold can be 14, 14.5, 15, or 15.5% AA+APM (relative to total $G_{M1}$ patterns).

An exemplary method for identifying fertility status of a human male individual comprises obtaining sperm samples, wherein the sperm samples are from the individual and wherein the sperm samples have been exposed to non-capacitating or capacitating conditions, fixed, and stained for $G_{M1}$. The frequency of selected $G_{M1}$ patterns in the sperm is determined. The frequency distributions for different $G_{M1}$ patterns in sperm exposed to non-capacitating and capacitating conditions is compared. A change in the frequency distribution of one or more selected $G_{M1}$ patterns in sperm exposed to capacitating conditions over sperm exposed to non-capacitating conditions is indicative of the fertility status of the individual. The $G_{M1}$ pattern can be selected from the group consisting of AA, APM, INTER, and combinations thereof.

An exemplary method for identifying fertility status of a male individual comprises obtaining a sperm sample, wherein the sperm sample is from the individual and wherein the sperm sample has been exposed to capacitating conditions, has been fixed and has been stained for the presence of $G_{M1}$. A frequency of selected $G_{M1}$ patterns in the sperm is determined. The frequency distributions for one or more different $G_{M1}$ patterns is compared to the frequency distributions from a control or predetermined criteria. The control sperm sample has been exposed to the same capacitating conditions and same fixative. A change in the frequency distribution of one or more selected $G_{M1}$ patterns relative to the change in the control is indicative of different fertility status of the individual than the fertility status of the control.

An exemplary method for identifying fertility status of a male individual comprises obtaining a sperm sample, wherein the sperm sample is from the individual, and wherein the sperm sample has been exposed to capacitating conditions, has been fixed, and has been stained for $G_{M1}$ patterns. The $G_{M1}$ distribution patterns in the sample are determined. The frequency of one or more $G_{M1}$ patterns is compared to an infertility threshold wherein a frequency less than the infertility threshold is indicative of fertility problems.

An exemplary kit for identifying fertility status of a male individual comprises one or more of the following: capacitating media, non-capacitating media, fixative composition, reagents for determining $G_{M1}$ staining patterns, comparison charts, predetermined criteria, representations of $G_{M1}$ patterns for comparison, or threshold values.

An exemplary method for measuring the fertility status of a male individual comprises obtaining a sperm sample, wherein the sperm sample is from the individual, and wherein the sperm sample has been exposed to capacitating conditions, has been exposed to a fixative, and has been stained for $G_{M1}$. Values are obtained for one or more of volume of the original sample, and concentration, motility, and morphology of the sperm in the original sample. A CAP score of the sperm sample is determined as the frequency of one or more $G_{M1}$ distribution patterns in the sample. A male fertility index (MFI) value of the individual is calculated based on the determined CAP score and the one or more obtained volume, concentration, motility, and morphology. For example, the MFI value can be calculated by multiplying the CAP score, the volume, the concentration, the motility value, and the morphology value. The motility can be a percentage of the sperm which are motile. The morphology can be a percentage of the sperm that are morphologically normal.

An exemplary method for measuring the fertility status of a male individual comprises obtaining a CAP score of a sperm sample of the individual as the frequency of one or more $G_{M1}$ distribution patterns in the sample. Values are obtained for one or more of volume of the original sample, and concentration, motility, and morphology of the sperm in the original sample. A male fertility index (MFI) value of the individual is calculated based on the determined CAP score and the one or more obtained volume, concentration, motility, and morphology.

The invention is further described through the following illustrative examples, which are not to be construed as restrictive.

Example 1

This example provides demonstration of $G_{M1}$ distribution patterns obtained with human sperm. Ejaculated sperm were collected from male donors, and allowed to liquefy for 20 mins at 37° C., and then volume, initial count, motility and morphology assessments were performed. 1 ml of the semen sample was layered on top of 1 ml of a density gradient (90% Enhance-S; Vitrolife, San Diego, Calif., USA) in a 15 ml conical tube. The tube was centrifuged at 300×g for 10 minutes. The bottom 1 ml fraction was transferred to a new 15 ml tube and then resuspended in 4 ml of mHTF. This was centrifuged at 600×g for 10 minutes. The supernatant was removed and the pellet of sperm was resuspended in 0.5 ml of mHTF. The washed sperm were then evaluated for concentration and motility. Equal volumes of sperm were then added to two tubes, such that the final volume of each tube was 300 µl, and the final concentration of sperm was 1,000,000/ml. The first tube contained mHTF (non-capacitating condition) and the second tube contained mHTF plus 2-hydroxy-propyl-β-cyclodextrin at a final concentration of 3 mM (capacitating condition). Sperm were incubated for varying lengths of time, but 3 hours was typically used. These incubations were performed at 37° C.

At the end of the incubation period, the contents of each tube were mixed gently, and 18 µl from each tube was removed and transferred to separate microcentrifuge tubes. 2 µl of 1% (weight/volume) paraformaldehyde was added to achieve a final concentration of 0.1%. In another embodiment, 0.1% (weight/volume) paraformaldehyde was added to achieve a final concentration of 0.01%. These tubes were mixed gently and incubated at room temperature for 15 minutes, at which time 0.3 µl of 1 mg/ml cholera toxin b subunit was added. The contents of the two tubes were again mixed gently and allowed to incubate for an additional 5 minutes at room temperature. From each tube, 5 µl was removed and placed on a glass slide for evaluation by fluorescence microscopy. To provide a counter-stain, speeding determination of focal planes and increasing longevity of the fluorescence signal, 3 µl of DAPI/Antifade was sometimes added.

Figure 2A:
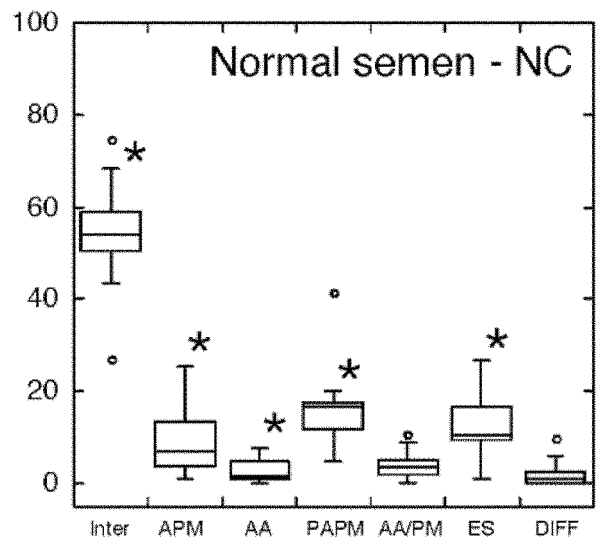
FIGS. 2A-2C show the relative distributions of the different localization patterns of $G_{M1}$ in normal human sperm under non-capacitating conditions (normal semen-NC.
Figure 2B:
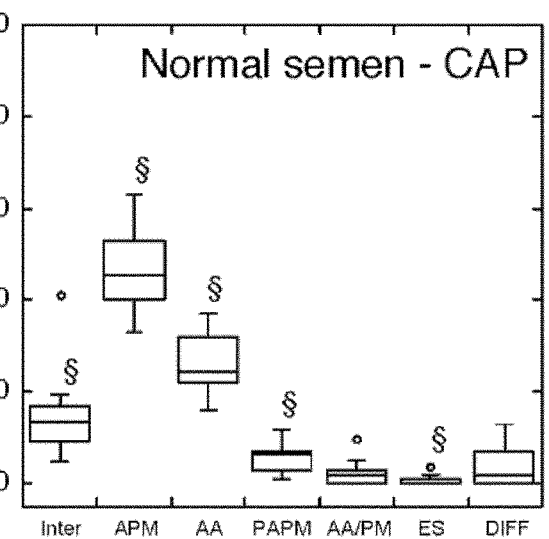
Figure 2C:
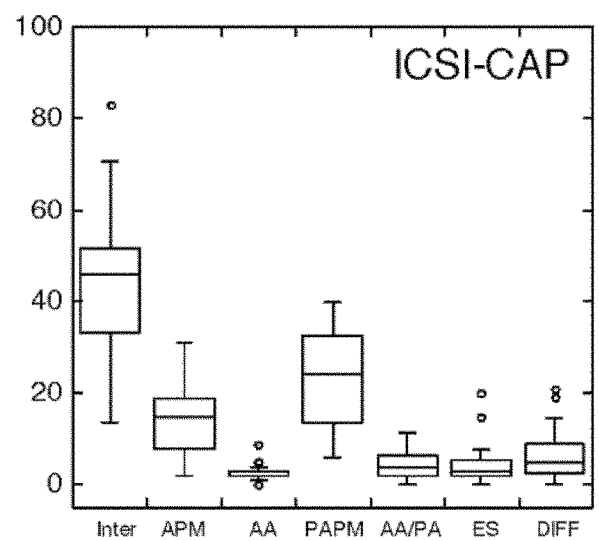

As shown in FIG. 2, localization patterns of $G_{M1}$ in normal human sperm reflect response to capacitating conditions. Full response is seen only in men with normal fertility; the responsive pattern was largely reduced or absent in men with unexplained infertility who have failed on previous attempts at intrauterine insemination (IUI) or in vitro fertilization (IVF). FIG. 1 shows the $G_{M1}$ patterns in human sperm. However, for the purpose of the diagnostic assay, patterns reflecting abnormalities such as PAPM, AA/PA, ES, and DIFF can be grouped for ease of analysis. FIGS. 2A-2C show the relative distributions of the different patterns in normal semen incubated under non-capacitating conditions (NC; FIG. 2A), or capacitating conditions (CAP; FIG. 2B). A reduction in INTER pattern is seen in normal semen upon exposure to CAP (FIG. 2C), while significant increases in the AA pattern and the APM pattern are also seen. In comparison with these normal data, sperm from a group of men known to have unexplained infertility were also subjected to the $G_{M1}$ assay. In these sperm, there was almost no increase in the AA pattern or the APM pattern under capacitating conditions.

Example 2

In this example, clinical histories of 34 patients were studied to perform a close analysis of their $G_{M1}$ assay scores relative to history of ever achieving clinical evidence of pregnancy. A male patient was defined as "fertile" if a patient couple achieved some evidence of fertilization/clinical pregnancy (even if limited to biochemical evidence or a sac without heartbeat on ultrasound) within 3 or fewer cycles.

Analysis of the data for these 34 patients revealed that if one applied a cut-off of 40% (APM+AA) for the score of the capacitated samples at the 3 hour time point, then 7/8 who "passed" (having a score of 39.5% or greater), were found to have been designated "fertile" (87.5%). Of the 26 who "failed" (having a score of 39.4 or less), only 3/26 had evidence of clinical pregnancy (11.5%). (see Table 1 below)

If one reduces the cutoff, it would be predicted that more people who are clinically sub-fertile will get a passing score and the percentage that pass the assay and are fertile within 3 cycles should go down. Interestingly, the result was not a smooth gradient or continuous curve in terms of fertility (as defined by the </=3 cycle criterion). That is, whether one failed the assay as defined at 40 or 35 didn't correlate with any significant change in chance of fertility, which was always low (between 11.5-14.3%). Conversely, passing the assay at 35 vs 40 corresponded with a very large difference in chances of fertility (ranging from 53.8-87.5%, respectively). To reinforce and reiterate this point, a change in 5% of the combined APM+AA percentages corresponded with over a 30% change in history of fertility.

These results suggest that male fertility is more like a "step function," in which ranges of scores for the male fertility assay correspond with categorizations of "fertile," "sub-fertile" or "infertile," rather than small changes in scores equating with correspondingly small but continuous changes in male fertility (chance of achieving clinical pregnancy). These data indicate strongly that a score of roughly 38.5-40 would be the cut-off between designations of "sub-fertile" or "fertile." Further examination of the data suggest that a cut-off of <14.5% could be used as a designation of likely "infertile."

| Cut-Off | Fertile Defined on Conceiving Within </= 3cycles | |
| --- | --- | --- |
| 39.5 | Pass | 8 (7/8 fertile = 87.5%) |
|  | Fail | 26 (3/26 fertile = 11.5%) |
| 38.5 | Pass | 8 (7/8 fertile = 87.5%) |
|  | Fail | 26 (3/26 fertile = 11.5%) |
| 37.5 | Pass | 11 (7/11 fertile = 63.6%) |
|  | Fail | 23 (3/23 fertile = 13.0%) |
| 36.5 | Pass | 11 (7/11 fertile = 63.6%) |
|  | Fail | 23 (3/23 fertile = 13.0%) |
| 35.5 | Pass | 13 (7/13 fertile = 53.8%) |
|  | Fail | 21 (3/21 fertile = 14.3%) |

Summarizing data for these men, who were all similar in terms of average semen parameters, suggest the following ranges (based on absolute scores): Infertile: <14.5, sub-fertile: 14.5-38.4, fertile: ≥38.5.

Figure 3:
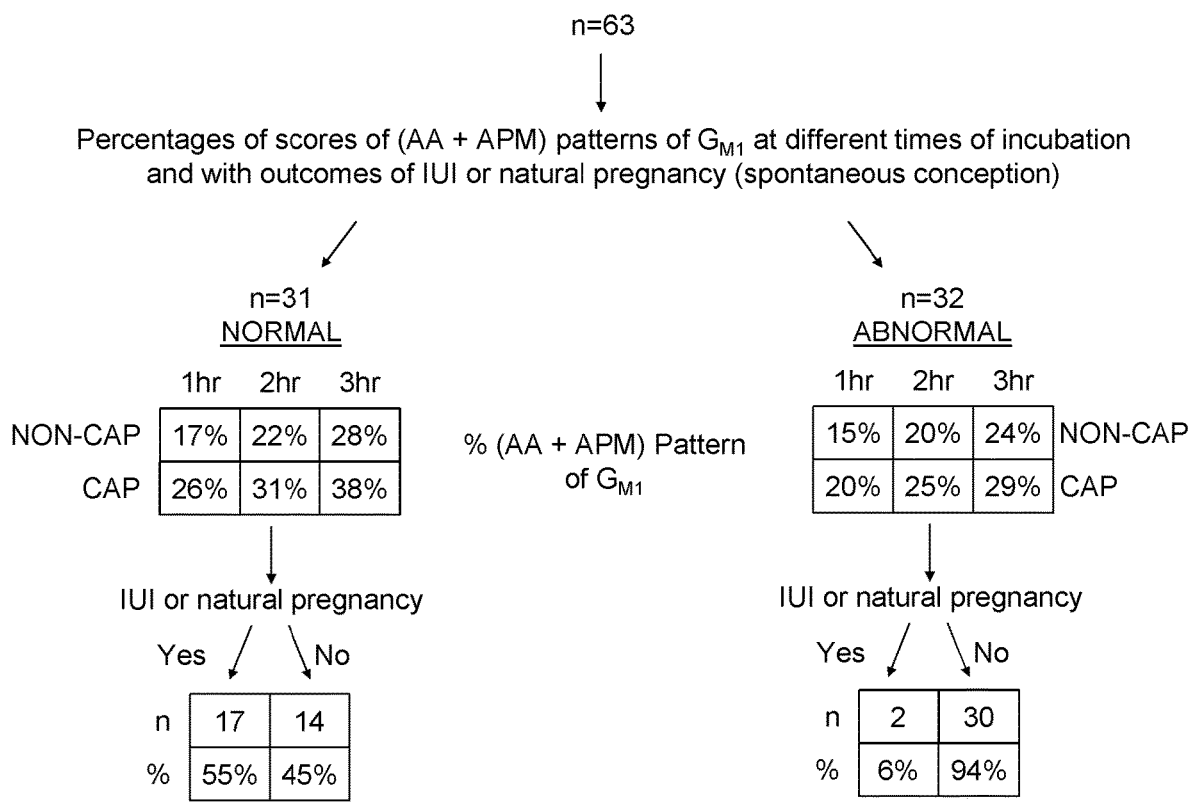
FIG. 3 shows the relative frequency of the combined APM and AA patterns as a function of time of incubation under capacitating conditions, or non-capacitating conditions. The clinical outcomes for those men whose samples were designated normal or abnormal are presented for each group.

Alternatively, one can evaluate the fertility of a sample by comparing the change in relative frequency of the APM and/or AA patterns over the time of incubation under capacitating conditions, or against the relative frequency observed under non-capacitating conditions. For example, one could compare the APM+AA relative frequency after 3 hours of incubation in capacitating conditions with the relative frequency of those patterns at the start of incubation. In yet another embodiment, one might compare the change in APM and/or AA frequencies with results obtained from successive time points (such as 1, 2, and 3 hours). In effect, one can plot the relative frequencies on the Y axis and time points on the X axis, and evaluate the slope or rate of change of the increasing frequency of one or more of the INTER, APM and/or AA samples under non-capacitating and capacitating conditions. When this approach to the analysis was performed in a group of 63 patients, 31 men with scores matching the normal reference group were identified, with baseline $G_{M1}$ patterns of 17%-22%-28% in non-capacitating and 26%-31%-38% in capacitating media, respectively over 1, 2, and 3 hours of incubation (see FIG. 3). 32 men with below reference values of 15%-20%-24% in non-capacitating and 20%-25%-29% in capacitating media were identified. Semen analysis parameters of number, motility and percent normal morphology (using strict WHO criteria) were comparable between the two groups. The population with normal range $G_{M1}$ patterns had an intrauterine insemination (IUI) pregnancy rate of 45.2% (14/31) of which 8 (25.8%) generated at least one fetal heartbeat. Three additional couples in this group became pregnant on their own. For men with below-reference $G_{M1}$ patterns, the IUI clinical pregnancy rate was only 6.3% (2/32; P=0.03). In this cohort, 13 underwent ICSI and 6 became pregnant (46.2%).

Although the present disclosure has been described with respect to one or more particular embodiments, it will be understood that other embodiments of the present disclosure may be made without departing from the spirit and scope of the present disclosure, and such other embodiments are intended to be within the scope of this disclosure.

What is claimed is:

1. A method for identifying fertility status of a human male individual comprising:
   obtaining a sperm sample from a human male;
   exposing said sperm to capacitating conditions in vitro to obtain capacitated sperm;
   fixing the in vitro capacitated sperm with a fixative;
   staining the in vitro capacitated and fixed sperm;
   identifying a capacitated state of the human male based on a sum percentage of apical acrosome (AA) $G_{M1}$ patterns;
   and a percentage of acrosomal plasma membrane (APM) $G_{M1}$ patterns in the in vitro capacitated, fixed, and stained sperm; and
   determining a fertility status of the human male by comparing the identified capacitated state to a predetermined fertility threshold based on a sum of a percentage of AA and a percentage of APM $G_{M1}$ patterns for a fertile population; and
   proceeding with a suitable assisted reproduction treatment to achieve fertilization based on the fertility status so determined, wherein the suitable assisted reproduction treatment comprises performing an intrauterine insemination (IUD), an in vitro fertilization (IVF) or an intra-cytoplasmic sperm injection (ICSI).

2. The method of claim 1, wherein the fixative comprises paraformaldehyde, glutaraldehyde or combinations thereof.

3. The method of claim 1, wherein the predetermined fertility threshold is the $G_{M1}$ distribution pattern percentage at which the fertility of a population ceases to substantially increase, and wherein a frequency less than the fertility threshold is indicative of infertile or sub-fertile fertility status.

4. The method of claim 1, wherein the predetermined fertility threshold is fertile fertility status.

5. The method of claim 1, wherein the predetermined fertility threshold is subfertile fertility status.

6. The method of claim 1, wherein the predetermined fertility threshold is infertile fertility status.

7. The method of claim 1, wherein the predetermined fertility threshold is a value obtained from a dataset comprising a plurality of individuals.

8. The method of claim 1, wherein the capacitating conditions to which the capacitated sperm have been exposed comprise:
   i) centrifugation of a sample comprising the sperm through a density gradient;
   ii) suspending a fraction of the density gradient comprising the sperm in a liquid comprising modified human tubal fluid (mHTF);
   iii) centrifugation of the fraction of ii) to obtain a pellet comprising the sperm;
   iv) suspending the pellet of iii) in a liquid comprising mHTF; and
   v) capacitating the sperm of iv) using 2-hydroxy-propyl-β-cyclodextrin.

9. A method for identifying fertility status of a human male individual comprising:
   exposing a sperm sample from the individual to capacitating conditions in vitro to obtain capacitated sperm;
   fixing the in vitro capacitated sperm with a fixative;
   staining the in vitro capacitated and fixed sperm;
   identifying $G_{M1}$ patterns, including induced apical acrosome (AA) $G_{M1}$ patterns and acrosomal plasma membrane (APM) $G_{M1}$ patterns;
   comparing a frequency of AA+(APM)$G_{M1}$ patterns in the in vitro capacitated, fixed, and stained sperm to a fertility threshold which is one standard deviation below a mean percentage of AA+APM $G_{M1}$ patterns for a fertile population,
   determining a fertile status of the human male when the frequency of AA+APM $G_{M1}$ patterns is greater than the fertility threshold, and determining an infertile or a sub-fertile status of the human male when the frequency of AA+APM $G_{M1}$ patterns is less than the fertility threshold; and
   proceeding with a suitable assisted reproduction treatment to achieve fertilization based on the infertile or sub-fertile status so determined, and wherein the suitable assisted reproduction treatment comprises an intrauterine insemination (IUI), an in vitro fertilization (IVF) or an intra-cytoplasmic sperm injection (ICSI).

10. The method of claim 9, further comprising:
    comparing the frequency of AA+APM $G_{M1}$ patterns in the capacitated sperm to an infertility threshold which is two standard deviations below the mean percentage of AA+APM $G_{M1}$ patterns for a fertile population; and
    determining a fertile status of the human male when the frequency of AA+APM $G_{M1}$ patterns is greater than the fertility threshold, and determining an infertile or a sub-fertile status of the human male when the frequency of AA+APM $G_{M1}$ patterns is less than the fertility threshold.

11. The method of claim 9, wherein exposing the sperm sample from the individual to capacitating conditions in vitro to obtain capacitated sperm comprises:
    i) centrifugation of a sample comprising the sperm through a density gradient;
    ii) suspending a fraction of the density gradient comprising the sperm in a liquid comprising modified human tubal fluid (mHTF);
    iii) centrifugation of the fraction of ii) to obtain a pellet comprising the sperm;
    iv) suspending the pellet of iii) in a liquid comprising mHTF; and
    v) capacitating the sperm of iv) using hydroxy-propyl-β-cyclodextrin.

* * * * *